(12) United States Patent
Tomomatsu

(10) Patent No.: US 6,727,993 B2
(45) Date of Patent: Apr. 27, 2004

(54) SURFACE INSPECTION INSTRUMENT AND SURFACE INSPECTION METHOD

(75) Inventor: Ryuzou Tomomatsu, Ichihara (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/147,520

(22) PCT Filed: May 14, 1998

(86) PCT No.: PCT/JP98/02119
§ 371 (c)(1),
(2), (4) Date: Feb. 22, 1999

(87) PCT Pub. No.: WO98/52025
PCT Pub. Date: Nov. 19, 1998

(65) Prior Publication Data
US 2002/0015148 A1 Feb. 7, 2002

(30) Foreign Application Priority Data
May 14, 1997 (JP) .............................................. 9-123987

(51) Int. Cl.[7] .............................................. G01N 11/30
(52) U.S. Cl. ..................................... 356/600; 356/237.2
(58) Field of Search .............................. 356/600, 237.2, 356/237.3

(56) References Cited

U.S. PATENT DOCUMENTS

| | | | | |
|---|---|---|---|---|
| 4,112,309 A | * | 9/1978 | Nakazawa et al. | 356/371 |
| 4,720,191 A | * | 1/1988 | Siegel et al. | 356/237.3 |
| 5,115,319 A | * | 5/1992 | Arai et al. | 348/230.1 |
| 5,523,846 A | * | 6/1996 | Haga | 356/600 |
| 5,706,091 A | * | 1/1998 | Shiraishi | 356/399 |
| 5,737,074 A | * | 4/1998 | Haga et al. | 356/237.3 |
| 5,745,236 A | * | 4/1998 | Haga | 356/371 |
| 5,963,314 A | * | 10/1999 | Worster et al. | 356/237.2 |

* cited by examiner

*Primary Examiner*—Richard A. Rosenberger
(74) *Attorney, Agent, or Firm*—Oblon, Spivak, McClelland, Maier & Neustadt, P.C.

(57) ABSTRACT

Apparatus for inspecting a surface of an object to be measured. The light source applies light to the surface. An objective lens opposite the surface receives reflected light. A light detector detects a component of the light incident on the lens from a direction parallel to its optical axis and obtains its light quantity. A slit is provided in the optical path between the objective lens and the detector in order to narrow the light detection extent in the surface to be measured. The surface condition of the object can be measured with a good accuracy independently of the shape of the object.

27 Claims, 4 Drawing Sheets

SURFACE INSPECTION INSTRUMENT AND SURFACE INSPECTION METHOD

BACKGROUND OF THE INVENTION

1. Field of the Invention

The present invention relates to a surface inspection apparatus and a surface inspection method, particularly to a surface inspection apparatus and a surface inspection method for measuring surface conditions of automobile parts, OA apparatus, household electric appliances or the like.

2. Discussion of the Background

In fields of trim parts of automobile, OA, domestic electrification or the like, the level of requirement for physical properties of the surfaces of products concerning their external appearances, in concrete terms, injuries, unevenness in height, unevenness in gloss, unevenness in color, and so forth, has become severer year by year. In particular, in products made of synthetic resins, in addition to the above-described various properties, the external appearance of a weld line, the external appearance of flow marks, stress whitening, and so forth, are greatly concerned in their commodity values.

The surface condition of such a product is hitherto appraised by performing a sensuous test, in which a classification is made on eye observation. In the sensuous test, however, the result of the test is obtained only in a rank on each appraisal item, and minute information on the surface condition, that is, information at the same level as a state of seeing with the naked eye can not be preserved, so it is a hindrance to quality control and material development.

In order to solve such a problem, it has been done to keep the surface condition of a product with a photograph or the like, but it is not considered objective data because its contrast varies according to photographing conditions, printing conditions, and so forth, so a method and an apparatus in which the surface condition of a product or a material can be accurately evaluated or measured have been desired earnestly.

On the other hand, as a method for measuring the surface condition of a synthetic resin material, the present applicant proposed a method for measuring the degree of whitening by an injury in the surface of the material (Japanese Patent Publication No. 52160/1995). This method is a method in which an injury of a predetermined shape is inflicted on a sample made of a synthetic resin, the injured whitening portion is irradiated with a light in dark-field illumination, and the light quantity of the component parallel with the optical axis of the objective lens in diffusedly reflected rays of the light is measured to measure the injury whitening degree. By changing the magnification of the objective lens according to the size of the injury, the light detection extent, that is, the extent in the surface of the sample subject to the measurement of the reflected light is controlled.

This method is useful for a material test in material development or the like, but has a problem that it can not be applied to surface inspection of products in quality control. That is, in this method, because an injury of a predetermined shape must be inflicted on a sample for measurement, the surface condition of the product can not be evaluated as it is, and further, because only the portion of the injury of the predetermined shape is measured due to the low detection accuracy, the surface condition of the whole of the object to be measured including the portion other than the injury can not be measured.

Besides, because an objective lens of a high magnification is used to decrease the detection extent when the whitening degree of a minute injury is measured, in case of a sample having a complicated shape, or the like, if the injury varies in position, a measurement error arises due to a divergence of the focus so a highly accurate measurement can not be realized. If an objective lens of a low magnification is used in order to decrease such a divergence of the focus, the peripheral portion of the injury is included in the detection extent, and so there is a problem that the reflected light from the injury can not be detected with a good accuracy.

SUMMARY OF THE INVENTION

It is an object of the present invention to provide a surface inspection apparatus and a surface inspection method in which the surface condition can be measured with a good accuracy independently of the shape of an object to be measured, and which can be applied also to surface inspection of products.

A surface inspection apparatus of the present invention is characterized by comprising a light source for applying a light to a surface of an object to be measured, an objective lens opposite to the surface of the object to be measured and for receiving a reflected light applied from the light source and reflected on the surface of the object to be measured, light detection means for detecting a component incident on the corresponding objective lens from a parallel direction with its optical axis in the reflected light passing through this objective lens and obtaining its light quantity, and a slit provided in the optical path between the objective lens and light detection means.

In the present invention, the light applied from the light source is reflected on the surface of the object to be measured, and the reflected light passes through the objective lens. When the reflected light is incident on the objective lens, the reflected light incident in parallel with the optical axis of the objective lens is incident on the slit after passing through the objective lens, and only the light having passed through the opening of this slit is introduced to the light detection means to obtain its light quantity.

In this manner, because the slit is provided in the light path between the objective lens and the light detection means, since only the component having passed through the opening of the slit in the reflected light reflected in the parallel direction with the optical axis of the objective lens can be taken out and detected, the detection extent of the reflected light in the surface of the object to be measured, namely, the light detection extent can be restricted by the opening of the slit. Accordingly, because the reflected light within the extent limited by narrowing the light detection extent with the objective lens and the slit can be taken out and its light quantity can be obtained, the surface condition of the aimed external appearance can be measured exactly and with a high accuracy.

Further, when the surface condition of the object to be measured of a complicated shape is measured, in case of using the objective lens of a low magnification for preventing a divergence of the focus, because the detection extent in the surface of the object to be measured can be restricted by the slit, since the surface of the object to be measured can be finely divided into a plurality of light detection extents and detected, the surface condition of the object to be measured can be measured with a good accuracy.

Because a superior detection accuracy can be obtained in this manner, not only the conventional degree of whitening of an injury but also a difference in the surface condition due to color, unevenness in height, or the like can be measured, and because the whole of the surface of the object to be measured including an uninjured portion can be measured, in addition to that an evaluation result corresponding to the external appearance of the object to be measured can be obtained, since it is avoided to inflict a predetermined injury on the surface of the object to be measured for measurement as a conventional manner, it can be applied to not only a surface inspection of a material but also a surface inspection in quality inspection of products.

Besides, when the object to be measured is evaluated with scanning, it is desirable to narrow the measurement area, that is, the light detection extent. At this time, because there is a fear of movement of focus with scanning, it is preferable for suppressing the movement of focus to narrow the light detection extent by using the objective lens of a magnification as low as possible and decreasing the opening of the slit.

Besides, because the objective lens of a lower magnification gets nearer to the external appearance of eye observation, a high correlation with the eye observation result can be obtained. Accordingly, it is desirable to use the objective lens of a low magnification, for example, not more than 10, particularly, 1 to 5.

Here, when the magnification is 1, a plane glass board merely transmitting light, an optical fiber cable or the like may be used as the objective lens, or the objective lens itself may not be used.

That is, it is a surface inspection apparatus characterized by comprising a light source for applying a light to a surface of an object to be measured, a tubular member, for example, an optical fiber cable opposite to the surface of said object to be measured and for receiving a reflected light applied from said light source and reflected on the surface of said object to be measured, light detection means for detecting a component incident on this tubular member from a specified direction in the reflected light and obtaining its light quantity, and a slit provided in the optical path between said tubular member and light detection means.

Further, in the apparatus of the present invention, if the spectral characteristic of the light source and the spectral sensitivity of the light detection means are provided into standard ones by selecting the light source and the light detection means, the light quantity can be obtained as a standardized value such as color-difference and lightness.

In the above, it is desirable that illumination switchover means is provided in the light path between the light source and object to be measured, and this illumination switchover means is to switch over bright-field illumination in which the light from the light source is made parallel with the optical axis of the objective lens and applied to the object to be measured through the objective lens, and dark-field illumination in which the light from the light source is made ringlike and applied obliquely with respect to the optical axis of the objective lens such that there is a focus on the surface of the object to be measured.

In this case, with the illumination switchover means, by properly using bright-field illumination and dark-field illumination according to the surface condition of the object to be measured or an aimed item to the surface condition, the surface condition of the object to be measured can be measured with a higher accuracy.

For example, in case of the object to be measured being made of a synthetic resin, when it is inspected on the presence of an injury, the size of the injury or the like, because the light becomes easier to be diffusedly reflected on the injury or the like by using dark-field illumination, in which the light is applied from an oblique direction, the detected light quantity increases and decreases greatly according to the injury, and a superior correlation with the eye observation result can be obtained. On the other hand, when it is inspected on unevenness in lightness, unevenness in gloss, the external appearance of a weld, the external appearance of flow marks, or the like, if bright-field illumination and dark-field illumination are selected according to the eye observation and used, a highly accurate inspection result corresponding to the eye observation can be obtained on each item.

Besides, in dark-field illumination, because the surface of the object to be measured is irradiated with the light in a ringlike manner from all directions, a measurement error due to difference in irradiation direction can be dissolved and a superior detection result correlated with the eye observation result can be obtained. That is, if the light is applied to the object to be measured only from one direction, because inferiority in the external appearance or the like has directivity in general, there is a case that the detected light quantity of the reflected light is different from the case of applying the light from the other direction, besides, because the direction of viewing the object to be measured in the eye observation judgement is not always fixed, by applying the light in the ringlike manner, scatter in data according to irradiation directions can be dissolved.

Further, when an abnormal portion in the surface of the object to be measured is measured by using dark-field illumination, it is desirable to set up the irradiation angle with the light with respect to the optical axis of the objective lens on the basis of the eye observation result. In concrete words, it is desirable that the abnormal portion of the object to be measured is observed with the naked eye with varying the angle, an angle condition in which a difference from the normal portion can be notably distinguished is selected, and this selected angle is used as the irradiation angle with the light. Thereby, because the surface condition can be observed under the same condition as the eye observation, a correlation with the eye observation result can be obtained.

It is desirable that the size of the opening of the above-mentioned slit is changeable.

Thereby, because the light detection extent in the surface of the object to be measured can be voluntarily controlled according to the surface condition of the object to be measured or the like by controlling the size of the opening of the slit, a more highly accurate inspection can be realized.

As the slit, for example, one having a circular opening can be used, and in this case, the diameter of the opening of the slit is desirably 0.2 to 30 mm. If the diameter of the opening of the slit is less than 0.2 mm, the light introduced into the light detection part is insufficient and there arises a fear that it becomes hard to measure.

Besides, when one on the surface of which uneven crimps are given is used as the object to be measured, it is preferable to broaden the light detection extent by increasing the diameter of the opening of the slit because a variation in measured value decreases.

Further, it is desirable that the above-mentioned light detection means comprises calculation means for converting the light quantity of the light having passed through the slit on the basis of a light quantity detected when a standard sample is used as the object to be measured.

Here, the standard sample is the sample used as a standard respectively in properties liked to inspect on the object to be measured, in concrete words, lightness, degree of white, color difference, or the like, for example, a standard sample that is made in common on the basis of a standard color chip of color such as white standard board and Munsell chroma, a standard sample set up individually, the normal portion in the object to be measured, or the like. This standard sample may be properly selected according to the evaluation item.

If such calculation means is provided, the light quantity detected on the object to be measured can be obtained as a relative value based on the light quantity of the standard sample. That is, not only an absolute measurement but also a comparative measurement can be performed. Accordingly, the inspection result can be obtained with a good reproducibility as a value near to the eye observation and easy to understand.

Besides, if one of a good eye observation result is used as the standard sample, because a relative inspection result based on this standard sample is obtained, the object to be measured can be evaluated with ease.

Further, when the inspections are performed with varying the measurement conditions, by using the same standard sample under each measurement condition and converting the light quantity of the object to be measured on the basis of the light quantity of this standard sample, because an error in the inspection result due to the difference in the measurement condition can be dissolved, an accurate inspection result is obtained.

On the other hand, a surface inspection method of the present invention is characterized in that a surface of an object to be measured is irradiated with a light and the irradiation light is reflected on the surface of the object to be measured, in this reflected light, a component parallel with the optical axis of an objective lens provided oppositely to the object to be measured is made incident on a slit through the objective lens, in this incident light, only a component having passed through an opening of said slit is received, and the light quantity of this received light is obtained.

In the present invention, since only the component having passed through the opening of the slit in the reflected light reflected in the parallel direction with the optical axis of the objective lens can be taken out and detected, the detection extent of the reflected light in the surface of the object to be measured, namely, the light detection extent can be restricted by the opening of the slit. Accordingly, because the reflected light within the extent limited by narrowing the light detection extent with the objective lens and the slit can be taken out and its light quantity can be obtained, the surface condition can be measured exactly and with a high accuracy.

Besides, even in case of using the objective lens of a low magnification, because the detection extent in the surface of the object to be measured can be restricted by the slit, the surface condition of the object to be measured can be measured with a good accuracy.

Further, because a superior detection accuracy can be obtained, not only the conventional degree of whitening of an injury but also even a shining injury (injury conspicuous due to increase in gloss of the injured portion, particularly, injury conspicuous upon holding the object to be measured to the light) can be measured. Besides, also a difference in the surface condition due to color, unevenness in height, or the like can be measured, and because the whole of the surface of the object to be measured including an uninjured portion can be measured, an evaluation result corresponding to the external appearance of the object to be measured can be obtained.

Further, since it is avoided to inflict a predetermined injury on the surface of the object to be measured for measurement as a conventional manner, it can be applied to not only a surface inspection of a material but also a surface inspection in quality inspection of products.

It is desirable that the light detection extent in the surface of the object to be measured is controlled by changing the size of the opening of the above-mentioned slit and the magnification of the objective lens, respectively.

Because the light detection extent in the surface of the object to be measured can be voluntarily controlled according to the surface condition of the object to be measured or the like by combining the size of the opening of the slit and the magnification of the objective lens in this manner, a more highly accurate inspection can be realized.

Further, it is desirable that the light quantity of the received light is converted on the basis of a light quantity detected when a standard sample is used as the object to be measured.

Thereby, because the light quantity of the light received on the object to be measured can be obtained as a relative value based on the standard sample, the reliability in the value of each measurement is high and the inspection result can be obtained with a good reproducibility as a value near to the eye observation and easy to understand.

Besides, if one of a good eye observation result is used as the standard sample, because a relative inspection result based on this standard sample is obtained, the object to be measured can be evaluated with ease.

Further, when the inspections are performed with varying the measurement conditions, by using the same standard sample under each measurement condition and converting the light quantity of the object to be measured on the basis of the light quantity of this standard sample, because an error in the inspection result due to the difference in the measurement condition can be dissolved, an accurate inspection result is obtained.

The irradiation angle with the light to the object to be measured may be changed according to the surface condition of the object to be measured.

There is no particular limit in this irradiation angle, and it may be voluntarily set up according to the object of the inspection and the surface condition of the object to be measured within a range of 0 to 45 degrees with respect to the optical axis of the objective lens.

By controlling the irradiation angle with the light in this manner, the surface condition of the object to be measured can be measured with a higher accuracy.

For example, when unevenness in gloss, the external appearance of a weld, flow marks, the presence of an injury, unevenness in height, or the like of the object to be measured made of a synthetic resin, if the irradiation angle with the light is selected by observing the object to be measured with the naked eye with varying the angle, a highly accurate inspection result corresponding to the eye observation can be obtained on each item.

DETAILED DESCRIPTION OF THE PREFERRED EMBODIMENTS

Hereinafter, an embodiment of the present invention will be described based on drawings.

Figure 1:
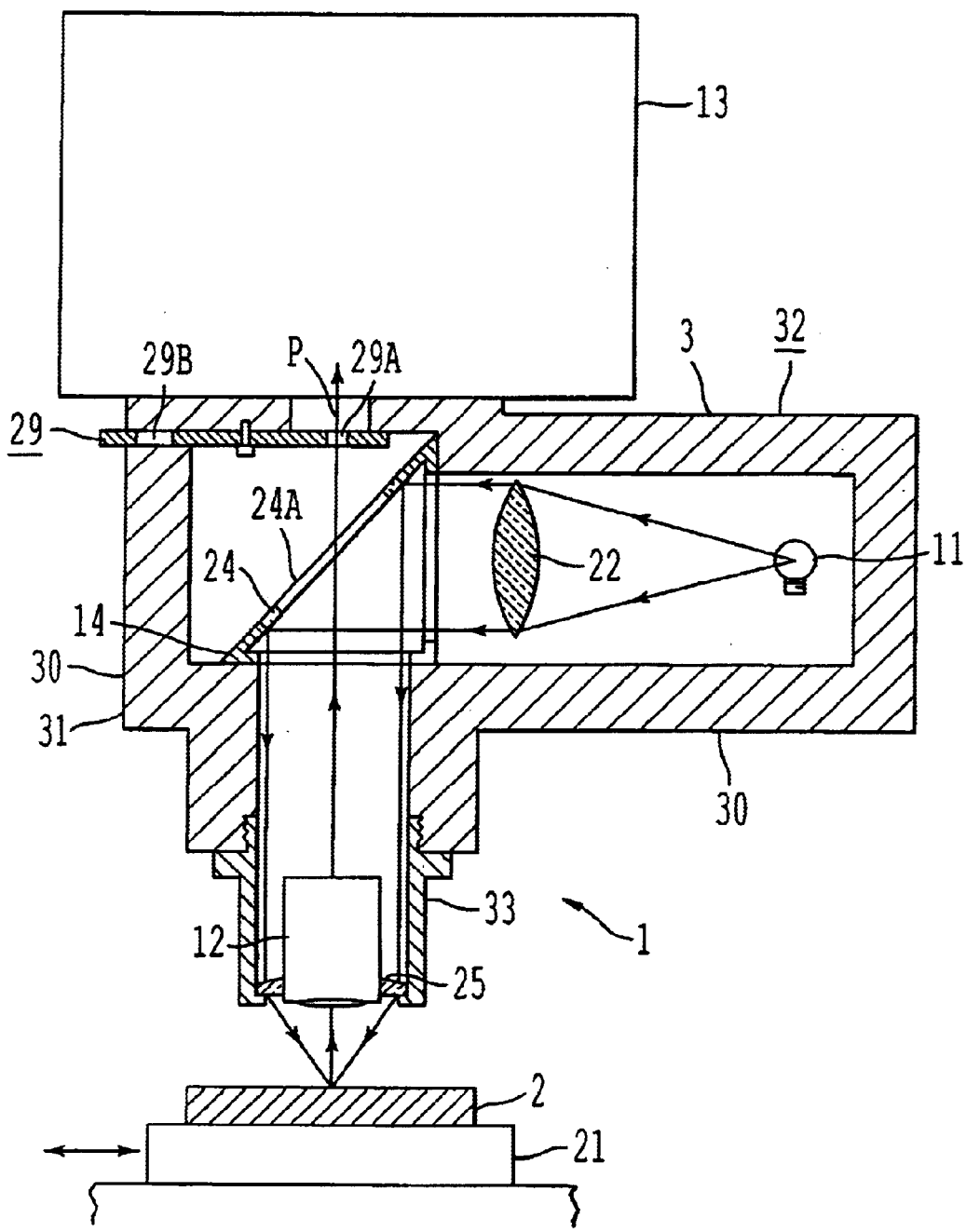
FIG. 1 is a view showing an embodiment of the present invention with its partial section.

In FIG. 1, a surface inspection apparatus 1 of this embodiment is shown. This surface inspection apparatus 1 comprises a light source 11 for applying a light to a surface of an object 2 to be measured, an objective lens 12 provided at the position opposite to the surface of the object 2 to be measured, and light detection means 13 for detecting a component incident on this objective lens 12 in a parallel direction with its optical axis to obtain the light quantity. In concrete terms, it is constructed by the manner that the light detection means 13 is connected to a polarizing microscope 3 of a reflected-illumination type including the light source 11 and the objective lens 12.

The microscope main body 30 of the polarizing microscope 3 comprises a tube 31 for vertical light path provided vertically and a tube 32 for illumination light path extending horizontally from the tube 31 for vertical light path. An objective lens barrel 33 is attached to the lower end portion of the tube 31 for vertical light path. This objective lens barrel 33 is attached perpendicularly to the axial line of the tube 32 for illumination light path.

In the interior of this objective lens barrel 33, the objective lens 12 is received, and a ringlike lens 25 for dark-field illumination, which will be described later, is received on the outer circumference of the objective lens 12. These objective lens 12 and lens 25 for dark-field illumination are put in with selectively combining one having a predetermined magnification and one having a predetermined refractive index, respectively. For such objective lens barrels 33, plural kinds of various magnifications of the objective lenses 12 and various refractive indices of the lenses 25 for dark-field illumination are provided, and by selectively mounting the objective lens barrel 33 on the tube 31 for vertical light path, the magnification of the objective lens 12 and the refractive index of the lens 25 for dark-field illumination in measurement can be adjusted.

Below this objective lens barrel 33, a stage 21 for putting the object 2 to be measured is provided. This stage 21 is disposed on the optical axis of the objective lens 12, and set so as to be movable horizontally and vertically.

The light source 11 is set on an axis perpendicularly intersecting the optical axis of the objective lens 12 in the interior of the tube 32 for illumination light path. On this axis, a collimate lens 22 for making a light from the light source 11 parallel rays perpendicularly intersecting the optical axis of the objective lens 12 is disposed.

Besides, at the position of an intersecting point between the optical axis of the light from the light source 11 and the optical axis of the objective lens 12 in the tube 31 for vertical light path, a bright/dark-field switchover slide 14, which is illumination switchover means for applying the light from the light source 11 to the object 2 to be measured as dark-field illumination or bright-field illumination, is set.

Figure 2:
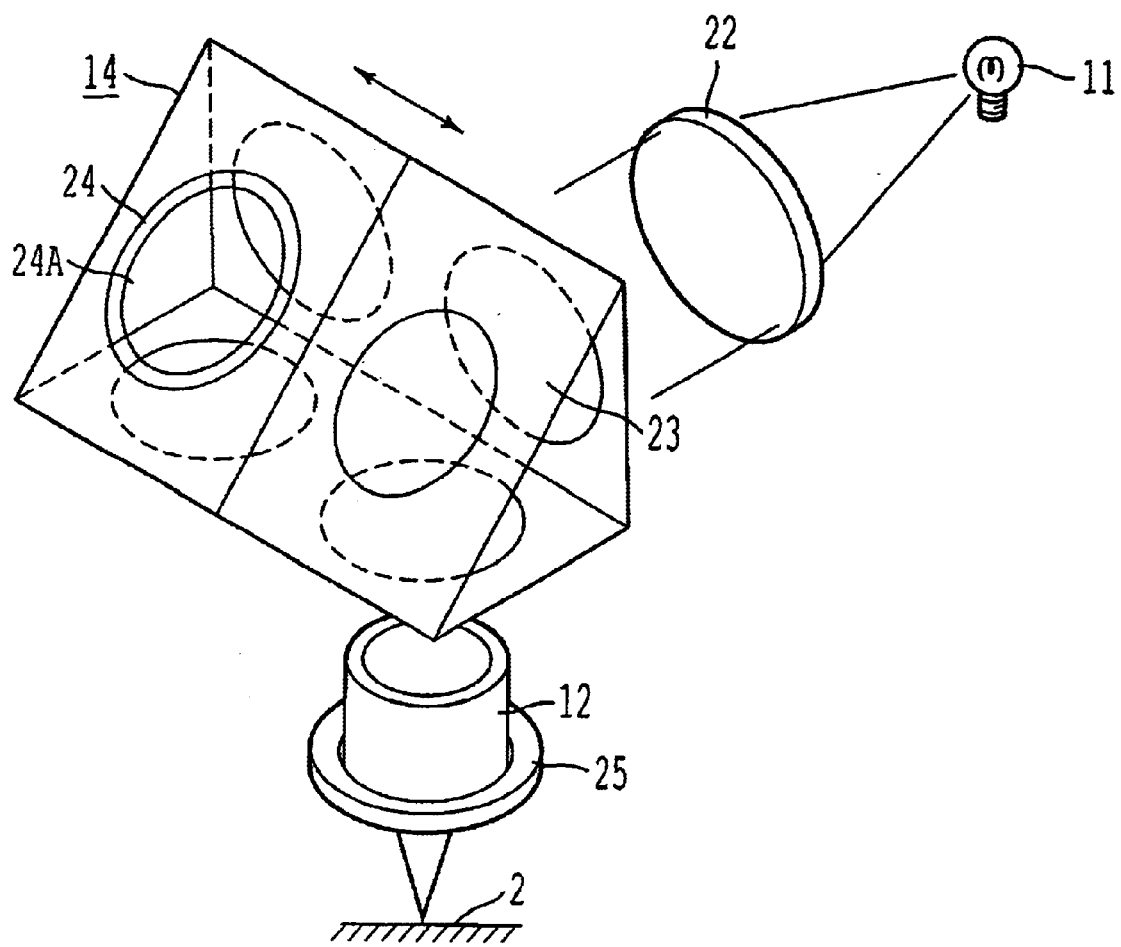
FIG. 2 is a perspective view showing illumination switchover means of the above embodiment.

As also shown in FIG. 2, this bright/dark-field switchover slide 14 is attached such that it can slide in the direction perpendicularly intersecting the optical axis of the light from the light source 11 and the optical axis of the objective lens 12. Along this slide direction, a circular half-mirror portion 23 for bright-field illumination and a ringlike fully-reflective-mirror portion 24 the inner portion of which is a light-pass portion 24A are provided in parallel. Besides, on the periphery of the objective lens 12, the ringlike dark-field illumination lens 25 is provided, and it is constructed such that the light reflected on the ringlike fully-reflective-mirror portion 24 in the direction of the optical axis of the objective lens 12 is applied from an oblique direction in order that there is a focus on the surface of the object 2 to be measured. For these dark-field illumination lenses 25, plural kinds of various refractive indices are provided, and by properly selecting and using these, the irradiation angle to the surface of the object 2 to be measured, namely, the irradiation angle with the light with respect to the optical axis of the objective lens 12 can be adjusted.

In such a polarizing microscope 3, by sliding the bright/dark-field switchover slide 14, bright-field illumination, in which the object 2 to be measured is irradiated with the light at the irradiation angle of zero degrees, and dark-field illumination, in which the object 2 to be measured is irradiated with the light at an oblique irradiation angle with respect to the optical axis of the objective lens 12, are switched over.

That is, as shown in FIG. 1, when the ringlike fully-reflective-mirror portion 24 for dark-field illumination is switched on the optical axis, only the light applied to the ringlike fully-reflective-mirror portion 24 in parallel rays from the collimate lens 22 is reflected to be formed into a ring shape and parallel with the optical axis of the objective lens 12, enters the dark-field illumination lens 25, and is refracted by an oblique angle with respect to the optical axis of the objective lens 12, for example, 45 degrees to be applied to the surface of the object 2 to be measured.

On the other hand, when the circular half-mirror portion 23 for bright-field illumination (refer to FIG. 2) is switched on the optical axis, only the light applied to the circular half-mirror portion 23 in parallel rays from the collimate lens 22 is reflected to be parallel with the optical axis of the objective lens 12, and applied through the objective lens 12 to the surface of the object 2 to be measured at the irradiation angle of zero degrees with respect to the optical axis of the objective lens 12.

Such a bright/dark-field switchover slide 14 is disposed on the same axial line as the objective lens 12 and stage 21. Above this bright/dark-field switchover slide 14, a barrel including an eyepiece not shown and the light detection means 13 are provided. These barrel (omitted in the drawing) and light detection means 13 are disposed on the optical axis of the objective lens 12.

In the apparatus 1 of this embodiment, the irradiation light applied to the surface of the object 2 to be measured from the light source 11 through the bright/dark-field switchover slide 14 is reflected on the surface of the object 2 to be measured to enter the objective lens 12. The component parallel with the optical axis of the objective lens 12 in the reflected light incident on this objective lens 12 is received by the light detection means 13.

In the light path between this light detection means 13 and the objective lens 12, in concrete words, between the light detection means 13 and the bright/dark-field switchover slide 14, a disclike slit 29 is set. This slit 29 is attached so as to be horizontally rotatable around its center. The slit 29 has a plurality of openings 29A and 29B different in size along its circumferential direction, and is attached such that these openings 29A and 29B are positioned on the optical axis of the objective lens 12 by rotation of the slit 29, respectively.

Thereby, by rotating the slit 29, the sizes of the openings 29A and 29B of the slit 29 on the optical axis of the objective lens 12 are changed to introduce only the light P having passed through the openings 29A and 29B on the optical axis to the light detection means 13.

Besides, in order to be operated for rotation from the outside of the microscope main body 30, the slit 29 is set such that its part projects outward beyond the tube 31 for vertical light path.

The shapes of the openings 29A and 29B of the slit 29 are not particularly limited and they may be circular ones or rectangular ones.

The above-described barrel (omitted in the drawing) including the eyepiece is provided below this slit 29, the size of the opening of the slit 29 is indicated in the visual field when the surface of the object 2 to be measured is observed through the eyepiece. Accordingly, as the surface of the object 2 to be measured is observed, the optimum opening of the slit 29 can be selected.

Figure 3:
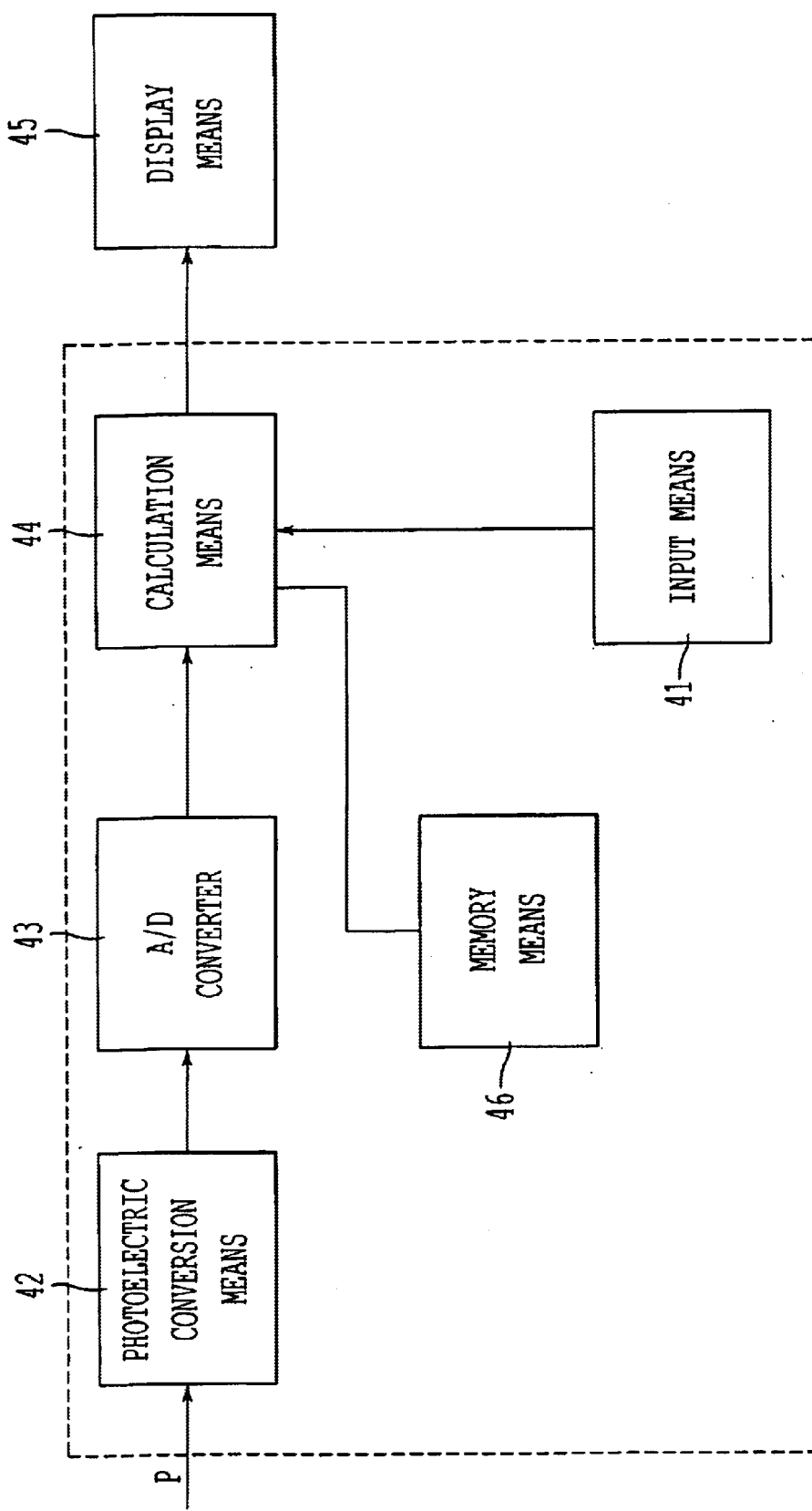
FIG. 3 is a block diagram showing light detection means of the above embodiment.

On the other hand, as shown in FIG. 3, the light detection means 13 is for receiving the light P having passed through the slit 29 to obtain its light quantity, and at need, converting this light quantity based on the light quantity of a standard sample.

This light detection means 13 comprises input means 41 for setting up the light quantity of the standard sample as a standard value, photoelectric conversion means 42 for converting the light quantity of the received light into an electric current value, an A/D converter 43 for digitizing the electric current value from this photoelectric conversion means 42, calculation means 44 for converting this digitized signal into a predetermined value. Display means 45 and memory means 46 are connected to this calculation means 44, and thereby, based on a setting-up command of the standard value from the input means 41, the light quantity of the object to be measured is calculated by the calculation means 44 according to data and a program stored in the memory means 46, and digitally displayed by the display means 45.

Next, a surface inspection method of this embodiment using the surface inspection apparatus 1 will be described.

First, the object 2 to be measured is put on the stage 21, and as the surface of the object 2 to be measured is observed through the eyepiece (omitted in the drawing), the magnification of the objective lens 12 is selected by changing the objective barrel 33, and the slit 29 is rotated to select the openings 29A and 29B disposed on the optical axis of the objective lens 12, and the light detection extent in the surface of the object 2 to be measured is controlled. In such a control of the light detection extent, the light detection extent restricted by the objective lens 12 is further restricted by the slit 29.

On the other hand, by sliding the bright/dark-field switchover slide 14 according to aimed items on the surface condition of the object 2 to be measured and the surface condition of the object 2 to be measured, illumination from the light source 11 is switched to bright-field illumination or dark-field illumination.

For example, in case of the object 2 to be measured being made of a synthetic resin, when it is inspected on items such as the presence of an injury and the size of the injury, in general, because the light is easier to be diffusedly reflected on the portion of the injury or the like when the light is applied from an oblique direction, dark-field illumination is used. On the other hand, when it is inspected on items such as unevenness in gloss, the external appearance of a weld, and flow marks, an angle at which a difference from the normal portion is obviously observed with the naked eye is selected, and bright-field illumination is used when this angle is zero degrees and dark-field illumination is used when it is an angle other than zero degrees. The light quantity is thereby accurately reflective of the surface condition of the object 2 to be measured on each item, and an inspection result corresponding to the eye observation can be obtained.

At this time, the irradiation angle with the light in dark-field illumination is made to correspond to the eye observation by setting up the refractive index of the lens 25 for dark-field illumination on the basis of the selected angle, and the irradiation angle is, for example, 45 degrees. Setting up the refractive index of the lens 25 for dark-field illumination is carried out by mounting the objective lens barrel 33 with the lens 25 for dark-field illumination of a desired refractive index onto the tube 31 for vertical light path.

When the light is applied from the light source 11, this irradiation light passes through the collimate lens 22 to be parallel rays, and is applied to the surface of the object 2 to be measured through the bright/dark-field switchover slide 14. This irradiation light is reflected on the surface of the object 2 to be measured, the component parallel with the optical axis of the objective lens 12 in this reflected light passes through the objective lens 12 to be incident on the slit 29, and only the component having passed through the openings 29A and 29B of the slit 29 in this incident light is detected by the photoelectric conversion means 42 of the light detection means 13 to convert its light quantity into an electric current value. This electric current value is digitized by the A/D converter 43, and when a calculation process is not performed, the electric current value is digitally displayed by the display means 45 as it is.

At this time, because the reflection angle of the light reflected on the surface of the object 2 to be measured, the intensity of the reflected light (reflectance) and the like vary according to the surface condition of the object 2 to be measured, the light quantity detected by the light detection means 13, namely, the displayed electric current value varies according to the surface condition of the object 2 to be measured.

For example, when there is a whitening injury (a crack due to surface chapping) in the surface of the object 2 to be measured, because the light applied to the portion of the injury is diffusedly reflected, between the portion of the injury and the portion where no injury is present, there is a difference in the light quantity incident on the objective lens 12 and passing through the slit 29, namely, in the detected light quantity.

Besides, when the color of the surface of the object 2 to be measured, in concrete terms, the hue, the lightness, the chroma or the like is variant, because the reflectance of the light varies, the detected light quantity varies according to the color of the surface of the object 2 to be measured.

When such an inspection is performed to a certain extent in the surface of the object 2 to be measured or the whole of the surface, namely, when it is evaluated with scanning, the inspection is performed as the object 2 to be measured is being moved by horizontally moving the stage 21 upon measurement, and the light is processed with sampling at regular periods in the light detection means 13. At this time, the stage 21 may be moved continuously or intermittently.

On the other hand, in case that the light quantity detected in the inspection of the object 2 to be measured is converted on the basis of the light quantity detected when the standard sample is used as the object to be measured, the surface condition of the standard sample is inspected beforehand like the above-described inspection of the object 2 to be measured, its light quantity is set up as the standard value by the input means 41 and stored in the memory means 46.

By the input means 41, it is set up to process to convert the light quantity of the object 2 to be measured on the basis of the stored standard value, and the surface condition of the object 2 to be measured is inspected. So, in the light detection means 13, the light quantity of the light received by the photoelectric conversion means 42 is converted into an electric current value, and the electric current value is digitized by the A/D converter 43 to be input to the calculation means 44. In this calculation means 44, the digitized electric current value is compared with the standard value stored in the memory means 46 to be calculated into a relative value, and this value is digitally displayed by the display means 45.

This standard sample is properly selected according to aimed items on the surface condition of the object 2 to be measured, an object of the inspection or the like.

For example, in case of a quality inspection of products or an inspection on an abnormal sample, a normal sample is used as the standard sample and a comparison result with the normal sample can be output. In concrete words, when a synthetic resin product is inspected with aiming items such as the lightness, the glossiness, the external appearance of a weld, and the external appearance of flow marks, by inspecting the product as the object to be inspected or the abnormal sample with the standard sample of the product with a good eye observation result on these items, the light quantities of these reflected lights are displayed as comparison results with the light quantity of the good product.

Besides, standardized one which becomes the base on an item aimed of inspection may be used as the standard sample. For example, when the color of the sample is evaluated, by using one generally used as a standard of object color, in concrete words, a color sample based on a standard chroma such as Munsell chroma as the standard sample, the light quantity of the object 2 to be measured as the inspection object is displayed as a difference in color from the standard sample.

Further, in one object 2 to be measured, when the evenness in its surface condition, in concrete words, unevenness in lightness, unevenness in gloss, unevenness in height, unevenness in color or the like is inspected, a predetermined portion in its surface may be used as the standard sample and the other portion may be measured with the standard value of the light quantity detected on this portion used as the standard sample. In this case, the detected light quantity is output as a difference from the light quantity of the portion used as the standard sample.

According to this embodiment as described above, there are the following effects.

That is, because the slit 29 is provided in the light path between the objective lens 12 and the light detection means 13, since only the component having passed through the opening 29A or 29B of the slit 29 in the reflected light reflected in the parallel direction with the optical axis of the objective lens 12 can be taken out and detected, the detection extent of the reflected light in the surface of the object 2 to be measured, namely, the light detection extent can be restricted by the opening 29A or 29B of the slit 29. Accordingly, because the reflected light within the extent limited by narrowing the light detection extent with the objective lens 12 and the slit 29 can be taken out and its light quantity can be obtained, the surface condition can be measured exactly and with a high accuracy.

In particular, when the surface condition of the object to be measured of a complicated shape is measured, in case of using the objective lens 12 of a low magnification for preventing a divergence of the focus, even in case of using no objective lens, because the detection extent in the surface of the object 2 to be measured can be restricted by the slit 29, since the surface of the object 2 to be measured can be finely divided into a plurality of detection extents and detected in the low magnification as it is, the surface condition of the object 2 to be measured can be measured with a good accuracy.

Further, because a superior detection accuracy can be obtained, not only the degree of whitening of an injury but also a difference in the surface condition due to color, gloss, unevenness in height, or the like can be measured, and because the whole of the surface of the object 2 to be measured can be measured, in addition to that an evaluation result corresponding to the external appearance of the object 2 to be measured can be obtained, since it is avoided to inflict a predetermined injury on the surface of the object 2 to be measured for measurement as a conventional manner, it can be applied to not only a surface inspection of a material but also a surface inspection in quality inspection of products.

Because the bright/dark-field switchover slide 14 is provided in the light path between the light source 11 and the object 2 to be measured, by properly using bright-field illumination and dark-field illumination correspondingly to the observation angle selected by observing the surface condition of the object 2 to be measured on a desired item with the naked eye, the surface condition of the object 2 to be measured can be measured with a higher accuracy.

Besides, in dark-field illumination, because the surface of the object 2 to be measured is irradiated with the light in a ringlike manner from all directions, a measurement error due to difference in irradiation direction can be dissolved and a superior detection result correlated with the eye observation result can be obtained. That is, if the light is applied to the object 2 to be measured only from one direction, there is a case that the detected light quantity is different from the case of applying the light from the other direction, besides, because the direction of viewing the object 2 to be measured in the eye observation judgement is not always fixed, by applying the light in the ringlike manner, scatter in data according to irradiation directions can be dissolved and the surface condition can be observed under the similar conditions to those of the eye observation.

By changing the magnification of the objective lens 12 and the sizes of the openings 29A and 29B of the slit 29, respectively, because the light detection extent in the surface of the object 2 to be measured can be controlled, an inspection with a higher accuracy can be realized.

Further, because the light detection means 13 has the calculation means 44, since the light quantity detected on the object 2 to be measured can be obtained as a value based on the light quantity of the standard sample, the inspection result can be obtained as the value close to the eye observation result and easy to understand.

Besides, by using one of a good eye observation result as the standard sample, because a relative inspection result based on this standard sample can be obtained, the object 2 to be measured can be evaluated with ease.

Further, even in case of inspecting with varying the measurement conditions, by using the same standard sample under each measurement condition and converting the light quantity of the object 2 to be measured on the basis of the light quantity of this standard sample, because error in inspection result due to difference in measurement condition can be dissolved, an accurate inspection result can be obtained.

Besides, because the surface inspection apparatus 1 is constructed by using the already present polarizing microscope 3, only by setting the slit 29 in the polarizing microscope 3 and connecting it to the light detection means 13, the apparatus 1 can be assembled with ease and at a low cost.

The present invention is not limited to the above embodiment, and contains other constitutions and the like that can attain the object of the present invention, and such modifications as shown below are also contained by the present invention.

Besides, although the slit in the above embodiment is formed into a disclike shape, it is not limited to this, for example, the slit may be formed into a beltlike shape, openings may be provided in parallel along its longitudinal direction, and the opening to be disposed on the optical axis of the objective lens may be selected by sliding the slit along the longitudinal direction, or a plurality of slits different in size of opening may be provided and the size of the opening on the optical axis may be changed by properly selecting and mounting this slit. Besides, the opening of the slit may be formed at a position being off the optical axis of the objective lens at need.

Although bright-field illumination and dark-field illumination are switched over by using the bright/dark-field slide 14 in the above embodiment, illumination switchover means is not limited to the construction using the bright/dark-field slide 14, for example, a construction using a slide different in shape from the slide 14 of the above embodiment may be employed, or fibers for illumination may be disposed annularly on the periphery of the objective lens to make dark-field illumination. After all, if bright-field illumination and dark-field illumination can be made, its construction is optional and an already present construction may be properly selected and used.

Besides, kinds of the light source and the light detection means are not particularly limited, for example, a light source and light detection means used in an already present calorimeter may be employed to construct a surface inspection apparatus for measuring color. As the already present calorimeter, for example, there are minute surface spectrocolorimeter MSP-Σ90 made by NIPPON DENSHOKUKOGYO CO., LTD., and so on.

By this manner, the light quantity of the object to be measured is obtained as a standardized value, in concrete words, the color of the surface of the object to be measured can be specified with L*a*b* color system, XYZ color system, or the like.

Otherwise, a light source and light detection means used in an already present lightness meter may be employed to construct a surface inspection apparatus for measuring lightness. By this, the light quantity of the object to be measured is obtained as a standardized lightness value.

After all, the kind and construction of the light detection means are not particularly limited if it can obtain the light quantity of the received light.

Besides, although the electric current value or the value into which the electric current value is converted is digitally displayed by the display means in the above embodiment, it may be displayed in an analogue form.

Although the surface inspection apparatus is constructed by using the already present polarizing microscope in the above embodiment, without using this polarizing microscope, the surface inspection apparatus may be constructed by assembling each part such as the light source, objective lens, light detection means and slit, etc.

Further, in the present invention, optical fiber cables can be utilized as follows.

That is, although the objective lens barrel 33 is used in the above embodiment, the objective lens barrel 33 can be changed to optical fiber cables. In this case, the light from the light source is introduced to optical fibers by a condensing lens. The optical fiber cables may be properly selected from among those used in general. For example, there are ones that the same quantity of plural fine optical fibers is bundled into each cable, respectively, and ones that one thick optical fiber is used as each cable. The optical fibers may be used in common for transmitting and receiving, but it is desirable to use them in the manner that ones for transmitting and ones for receiving are distinguished from each other. In this case, the optical fibers on the light source side, in order that the light condensed through the condensing lens from the light source enter, and in order to introduce only the light through the optical fibers for receiving in the reflected light from the object to be measured to the slit, the optical fibers for transmitting and receiving are desirably used with being bundled, respectively. On the other hand, on the object-to-be-measured side, in order that the light applied to the object to be measured from the optical fibers and the reflected light entering the optical fibers from the object to be measured are evenly distributed within the measurement extent, it is desirable randomly to bundle the optical fibers for transmitting and receiving, respectively. In case of using a plurality of optical fibers in the manner that ones for transmitting and ones for receiving are distinguished from each other, there is no particular limit in the proportion of the numbers used respectively but it is desirable to use almost the same number of optical fibers. Besides, it is desirable to attach tubular attachments to the other ends of the optical fibers. By contacting the tips of the attachments with the surface of the object to be measured, the measurement can be performed with keeping constant the distance from the object to be measured or the irradiation angle of the object to be measured with the light. The shape of the attachment is not particularly limited if it is a shape that the light applied from the optical fibers reaches the surface of the object to be measured and the reflected light reaches the optical fibers, and may be cylindrical, fanwise, or a skeleton construction that the wall surface of a cylinder is open.

Besides, the objective lens barrel 33 may be attached to the tips of the optical fibers for measuring the surface condition with a still higher accuracy. Even in this case, it is desirable to attach the above attachment to the tip of the objective lens barrel 33.

By using such flexible and long optical fibers, without putting the object to be measured on the stage 21, its surface condition can be measured. Accordingly, the measurement is possible independently of the size of the object to be measured and the place of measurement. For example, even a particularly large-sized final product, or one being at a job site such as a factory at a long distance from the main body of the measurement apparatus can be measured.

Further, if a network of optical fiber cables is laid in advance in a wide area such as a laboratory and a factory, if the measurement part comprising the optical fibers and the attachments, and, according to circumstances, the objective lens barrel is separately manufactured to be portable, it is also possible freely to measure in the network. Otherwise, if the measurement apparatus itself is constructed compactly, it is also possible to provide a portable handy-type measurement apparatus.

In case of carrying it using the optical fibers, the measurement is possible independently of the size of the object to be measured and the place of measurement. By attaching the attachments to its most headed end, it is also possible to provide a portable handy-type measurement apparatus.

Besides, the objective lens attached to the objective lens barrel 33 may be a plane lens of the magnification of 1. In case of the magnification of 1, the objective lens itself becomes needless, but it is desirable to attach the plane glass to the attachment position of the objective lens for protecting the light source 11 and the light detection means 13 from dust and other substances floating in air.

The kind of the object to be measured, in concrete words, the quality of the material, shape, size, color, or the like is optional.

Example

Using samples made of a synthetic resin as the object 2 to be measured in the above embodiment, gloss of injury, unevenness in gloss and external appearance of weld line were evaluated, respectively.

[Evaluation of Gloss of Injury]

Evaluations of gloss of injury were made on four samples A to D provided with different injuries from one another.

The sample A was obtained in the manner that a flat-boardlike test piece (120 mm×120 mm×3 mm) made of a polypropylene resin composition in which 23 wt. % of talc, 4 wt. % of ethylene-propylene elastomer and 1.3 wt. % of a pigment (dark gray) were mixed, was prepared and an injury of a length of 50 mm was inflicted on this test piece with a taper scratch tester made by TOYO SEIKI, LTD.

Inflicting the injury on the test piece was performed by using a cylindrical metal stick of a diameter of 3 mm, the outer circumference of the tip surface of which was beveled in 4 mmR, in place of a cutter for inflicting, with applying a load of 20 gf. When the injury is inflicted with such a metal stick, the injured portion becomes smooth and the glossiness becomes higher than that before it is injured.

The sample B was obtained in the same manner as the sample A but applying a load of 100 gf when an injury was inflicted on the test piece.

The sample C was obtained in the same manner as the sample A but applying a load of 300 gf when an injury was inflicted on the test piece.

The sample D was obtained in the same manner as the sample A but applying a load of 500 gf when an injury was inflicted on the test piece.

<Measurement Example>

As for these four samples A to D, surface inspections were performed with the surface inspection apparatus 1 of the above embodiment. These inspections were performed respectively to the injured portion on which the injury had been inflicted and an uninjured portion where there was no injury, in each surface of the samples A to D. The measurement conditions were as follows;

magnification of objective lens: 5 opening of slit: circle of diameter of 2 mm kind of illumination: dark-field illumination (irradiation angle of 45 degrees).

In these inspections, detected light quantities were displayed as follows. That is, an inspection of a white standard board was performed in advance under the same measurement conditions as the samples A to D, and the detected light quantity of the white standard board was used as a standard value, and the light quantities detected in the inspections of the samples A to D were converted with considering the standard value the base of 100%, and displayed. The results are shown in a table 1.

<Comparative Example>

On the other hand, measurements were performed respectively on the injured portions and the uninjured portions of each of the samples A to D by the method of the Japanese Patent Publication No. 52160/1995, and the light quantities of the reflected lights were obtained as exposure times of a camera. The results are shown in the table 1.

Injury's hardness to be conspicuous was evaluated on each of the samples A to D by eye observation, and ranked in order of the hardness to be conspicuous decreasing. The results are shown in the table 1.

TABLE 1

| | Injuring load (gf) | Order of hardness to be conspicuous by eye observation | Comparative example | | | Measurement example | | |
|---|---|---|---|---|---|---|---|---|
| | | | Exposure time of uninjured portion (sec) | Exposure time of injured portion (sec) | Difference in exposure time (%) | Uninjured portion (%) | Injured portion (%) | Difference (%) |
| A | 20 | 1 | 10 | 10 | 0 | 7.0 | 6.7 | 0.3 |
| B | 100 | 2 | 10 | 10 | 0 | 6.8 | 6.4 | 0.4 |
| C | 300 | 3 | 10 | 10 | 0 | 6.4 | 5.7 | 0.7 |
| D | 500 | 4 | 10 | 10 | 0 | 7.1 | 6.0 | 0.9 |

As shown in the table 1, it is understood that, by performing the surface inspection with the surface inspection apparatus 1 of the above embodiment, the difference in gloss between the injured portion and the uninjured portion can be clearly detected and a highly accurate inspection result corresponding to the eye observation result can be obtained.

On the other hand, by the method of the Japanese Patent Publication No. 52160/1995, there was found no difference in exposure time between the injured portion and the uninjured portion, and no correlation with the eye observation result was obtained. It is thus understood that the method of the above embodiment can realize a surface inspection with a higher accuracy than the method of the Japanese Patent Publication No. 52160/1995.

[Evaluation of Unevenness in Gloss]

Evaluations of unevenness in gloss were made with the surface inspection apparatus 1 of the above embodiment on car bumpers manufactured by injection molding with the same resin as the above-mentioned samples A to D.

That is, three bumpers were prepared as samples E to G, and an extent of 13 mm×31 mm including an unevenness portion in gloss arising on the lower side of a logo formed on each of the samples E to G, that is, on the lower side of the resin flow, was used as a measurement region. These measurement regions were at the same position as one another in the samples E to G.

The measurement conditions were as follows;

magnification of objective lens: 5 opening of slit: circle of diameter of 5 mm kind of illumination: bright-field illumination (irradiation angle of zero degrees).

In these inspections, the light detection extent by the surface inspection apparatus 1 was narrowed into an extent of 1 mm square within the above-mentioned measurement region, and the surface in the measurement region was scanned by inspecting by the extents of 1 mm square with intermittently moving the sample 1 mm at a time. The detected light quantities were displayed after converting into the rates (%) when the light quantity of the white standard board (standard sample) was 100%, like the above-mentioned samples A to D.

The maximum value, the minimum value and the difference between them in each measurement region of the samples E to G are shown in a table 2.

TABLE 2

|  | Maximum value (%) | Minimum value (%) | Difference (%) |
|---|---|---|---|
| Sample E | 11.0 | 6.3 | 4.7 |
| Sample F | 14.7 | 6.1 | 8.6 |
| Sample G | 10.7 | 5.0 | 5.7 |

As shown in the table 2, from the fact that the difference between the maximum value and the minimum value in the measurement region of the sample E is little in comparison with those of the samples F and G, it is understood that the sample E is a sample of a little unevenness in gloss. On the other hand, the difference between the maximum value and the minimum value of the sample G is the greatest among the three samples E to G, and it is understood that it is a sample of a great unevenness in gloss.

In this manner, it is understood that, by performing the surface inspection with the surface inspection apparatus 1 of this embodiment, the unevenness in gloss in a predetermined measurement region can be measured with a high accuracy.

[Evaluation of External Appearance of Weld Line]

Evaluations of external appearance of weld line were made with the surface inspection apparatus 1 of the above embodiment on flat-boardlike samples H and I on the surfaces of which crimps (pattern by unevenness in height) are given. These samples H and I were made of molds by injection molding in the middles of which rectilinear weld lines were formed, and the sample H has a conspicuous weld line and the sample I has a hardly conspicuous weld line. The measurement conditions in these inspections were as follows;

magnification of objective lens: 5 opening of slit: circle of diameter of 5 mm kind of illumination: bright-field illumination (irradiation angle of zero degrees).

In these inspections, a region of 20 mm×1 mm perpendicularly intersecting the weld line was used as a measurement region in each surface of the samples H and I, and the weld lines were positioned in the middle portions of the measurement regions, respectively. The measurement regions of the samples H and I were set up to be at the same position as each other.

The surface inspection on each measurement region was performed by scanning with moving the samples H and I similarly to the time of performing the above-mentioned evaluations of unevenness in gloss (samples E to G). That is, the light detection extents in the surfaces of the samples H and I were narrowed into extents of 1 mm square, and the inspection was performed by the extents of 1 mm square with intermittently moving the sample 1 mm at a time in the longitudinal direction of the measurement region, that is, rectilinearly in the direction perpendicular to the weld line.

In these inspections, the detected light quantities were displayed after converting into the rates (%) when the light quantity of the white standard board (standard sample) was 100%, like the above-mentioned samples A to D and E to G. The results are shown in FIG. 4.

Figure 4:
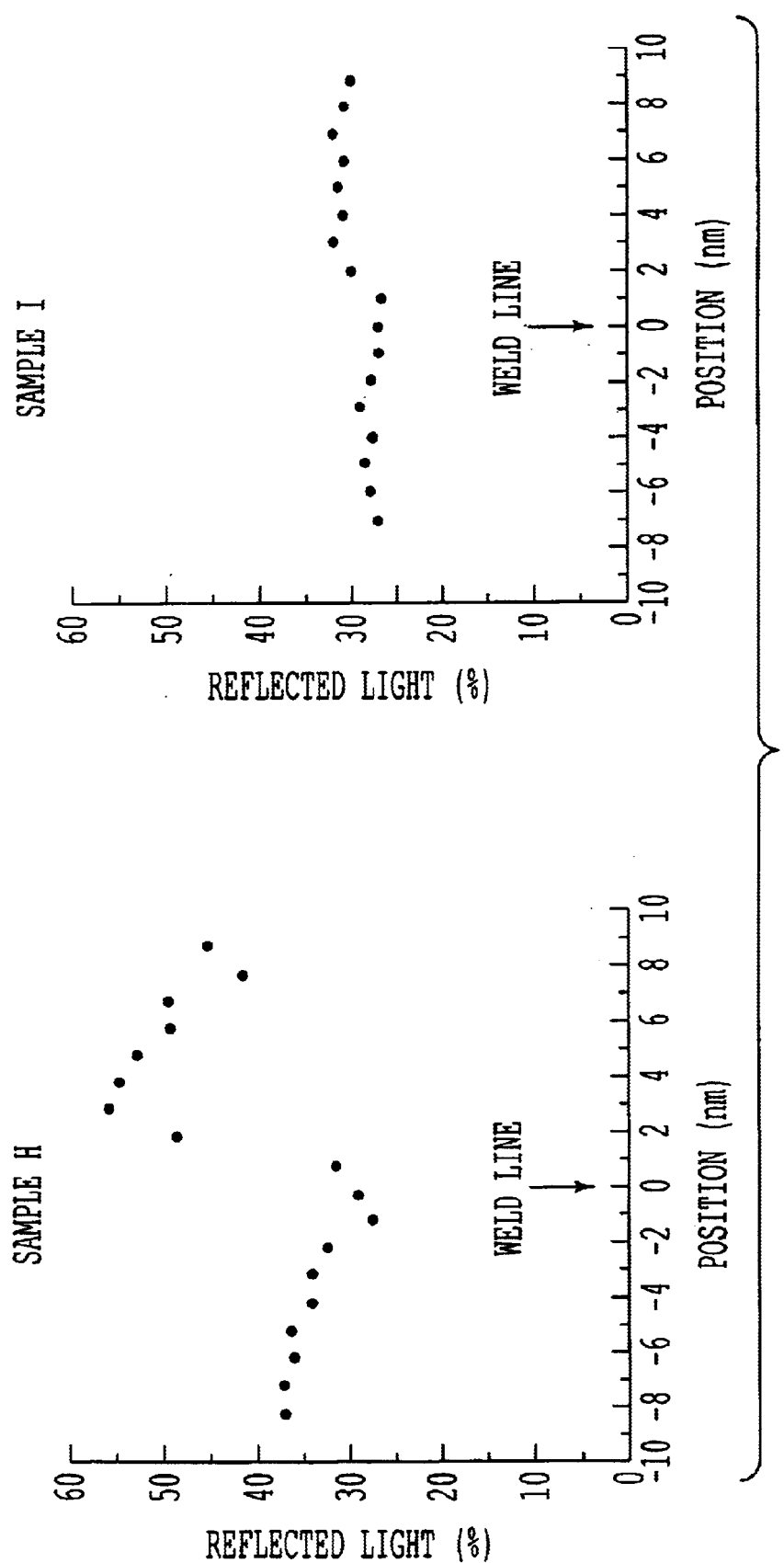
FIG. 4 is a view showing a result that the external appearance of a weld line is inspected with the surface inspection apparatus of the above embodiment.

By FIG. 4, it is understood that the reflected light on the surface of the sample H varies more widely than that of the sample I and the weld line of the sample H is more conspicuous than that of the sample I. In this manner, it is understood that, by performing the surface inspection with the surface inspection apparatus 1 of this embodiment, the external appearance of the weld line, that is, easiness to be conspicuous can be detected as a difference in reflected light from the peripheral portion and a highly accuracy inspection result corresponding to the eye observation result can be obtained.

Possibility of Industrial Utilization

As described above, according to the present invention, by providing a slit in the optical path between an objective lens for receiving a reflected light reflected on a surface of an object to be measured, and light detection means for detecting a component incident on this objective lens in a parallel direction with its optical axis, and obtaining its light quantity, and taking out only a component having passed through an opening of the slit to detect, because the detection extent of the reflected light in the surface of the object to be measured, that is, the light detection extent can be restricted with the opening of the slit, the surface condition can be measured exactly and with a high accuracy.

Further, even in case of using the objective lens of a low magnification, because the detection extent in the surface of the object to be measured can be restricted by the slit, since the surface of the object to be measured can be finely divided into a plurality of light detection extents and detected, the surface condition of the object to be measured can be measured with a good accuracy.

Besides, because a superior detection accuracy can be obtained, not only the conventional degree of whitening of an injury but also a difference in the surface condition due to gloss, color, unevenness in height, or the like can be measured, and because the whole of the surface of the object to be measured including an uninjured portion can be measured, in addition to that an evaluation result corresponding to the external appearance of the object to be measured can be obtained, since it is avoided to inflict a predetermined injury on the surface of the object to be measured for measurement as a conventional manner, it can be applied to not only a surface inspection of a material but also a surface inspection in quality inspection of products.

What is claimed is:

1. A surface inspection method using a surface inspection apparatus, the surface inspection apparatus comprising:

a light source structurally configured to apply a light to a surface of an object to be measured;

an objective lens structurally configured to receive a reflected light applied from the light source and reflected on the surface of the object to be measured, the objective lens being located at a position opposite to the surface of the object to be measured;

an illumination switchover member structurally configured to switch over both bright-field illumination and dark-field illumination, the bright-field illumination being that in which the light from the light source is made parallel with an optical axis of the objective lens and applied to the object to be measured through the objective lens, and the dark-field illumination being that in which the light from the light source is made ring-shaped and applied obliquely with respect to the optical axis of the objective lens such that there is a focus on the surface of the object to be measured, and the illumination switchover member being provided in a light path between the light source and the object to be measured;

a light detection member structurally configured to detect a component incident on the objective lens from a parallel direction with the optical axis of the objective lens in the reflected light received by the objective lens and obtaining a light quantity thereof; and a rotatable disc-shaped plate having a plurality of openings of different sizes, the plate provided in an optical path between the objective lens and the light detection member, and the openings controlling the quantity of light passing through the plate into the light detection member; and the surface inspection method characterized by the steps of observing an abnormal portion of the object to be measured with a naked eye of a user of the surface inspection apparatus while varying an angle in which a difference from a normal portion is observed, selecting a condition of the angle in which the difference from the normal portion can be notably distinguished, and using the selected condition of the angle as an irradiation angle for the light, wherein the illumination switchover member comprises a bright-field/dark-field illumination switchover slide that slides in a direction perpendicular to both an optical axis of a collimate lens for refracting light from the light source and perpendicular to an optical axis of the objective lens, and along the sliding direction, a circular half-mirror portion for the bright-field illumination and a ring-shaped fully-reflective-mirror portion for the dark-field illumination are provided in parallel with each other, an inner portion of the ring-shaped fully-reflective-mirror portion for the dark-field illumination being a light-pass portion, such that on a periphery of the objective lens, a ring-shaped dark-field illumination lens is provided, and the ring-shaped dark-field illumination lens is structurally configured such that light reflected on the ring-shaped fully-reflective-mirror portion in a direction of the optical axis of the objective lens is refracted by the ring-shaped dark-field illumination lens in an oblique direction toward the surface of the object to be measured.

2. The surface inspection method according to claim 1, wherein:

in the ring-shaped dark-field illumination lens, plural kinds of various refractive indices are provided, and by properly selecting and using the plural kinds of various refractive indices, either the irradiation angle to the surface of the object to be measured or the irradiation angle for the light with respect to the optical axis of the objective lens can be adjusted.

3. The surface inspection method according to claim 1, wherein the dark-field illumination is employed by the illumination switchover member.

4. The surface inspection method according to claim 1, wherein the light detection member comprises a calculation member structurally configured to convert a light quantity of a light having passed through one of a plurality of openings in the rotatable disc-shaped plate on a basis of a light quantity detected when a standard sample is used as the object to be measured.

5. The surface inspection method according to claim 1, wherein the surface of the object to be measured is irradiated with a light to produce an irradiation light so that the irradiation light is reflected on the surface of the object to be measured to produce a reflected light, and in the reflected light, a component parallel with the optical axis of the objective lens which is provided at the position opposite to the object to be measured is made incident on the rotatable disc-shaped plate through the objective lens to produce an incident light, and in the incident light, only a component having passed through one of a plurality of openings of the rotatable disc-shaped plate from the objective lens is received to produce a received light, and a light quantity of the received light is obtained.

6. The surface inspection method according to claim 5, wherein a light detection extent in the surface of the object to be measured is controlled by changing a size of one of the plurality of openings of the rotatable disc-shaped plate and a magnification of the objective lens.

7. The surface inspection method according to claim 5, wherein the light quantity of the received light is converted on a basis of a light quantity detected when a standard sample is used as the object to be measured.

8. The surface inspection method according to claim 1, wherein the surface of the object to be measured is irradiated with a light to produce an irradiation light so that the irradiation light is reflected on the surface of the object to be measured to produce a reflected light, and in the reflected light, only a component which is in almost one direction is made incident on the rotatable disc-shaped plate through a tubular member to produce an incident light, and in the incident light, a light quantity of only a component having passed through one of a plurality of openings of the rotatable disc-shaped plate from the tubular member is obtained.

9. The surface inspection method according to claim 8, wherein a light detection extent in the surface of the object to be measured is controlled by changing a size of one of the plurality of openings of the rotatable disc-shaped plate and a magnification of the objective lens.

10. The surface inspection method according to claim 1, wherein the surface of the object to be measured is irradiated with a light to produce an irradiation light such that the irradiation light is reflected on the surface of the object to be measured to produce a reflected light, and the reflected light is made incident on the rotatable disc-shaped plate through an optical fiber cable to produce an incident light, and in the incident light, a light quantity of only a component having passed through one of a plurality of openings of the disc-shaped plate from the optical fiber cable is obtained.

11. The surface inspection method according to claim 10, wherein a light detection extent in the surface of the object to be measured is controlled by changing a size of one of the openings of the rotatable disc-shaped plate and a magnification of the objective lens.

12. The surface inspection method according to claim 1, wherein the object to be measured is made of a synthetic resin.

13. A surface inspection method using a surface inspection apparatus, the surface inspection apparatus comprising:

light source applying means for applying a light to a surface of an object to be measured;

objective lens receiving means for receiving a reflected light applied from the light source applying means and reflected on the surface of the object to be measured, the objective lens receiving means being located at a position opposite to the surface of the object to be measured;

illumination switchover means for switching over both bright-field illumination and dark-field illumination, the bright-field illumination being that in which the light from the light source applying means is made parallel with an optical axis of the objective lens receiving means and applied to the object to be measured through the objective lens receiving means, and the dark-field illumination being that in which the light from the light source applying means is made ring-shaped and applied obliquely with respect to the optical axis of the objective lens receiving means such that there is a focus on the surface of the object to be measured, and the illumination switchover means being provided in a light path between the light source applying means and the object to be measured;

light detection means for detecting a component incident on the objective lens receiving means from a parallel direction with the optical axis thereof in the reflected light received by the objective lens receiving means and obtaining a light quantity thereof; and a rotatable disc-shaped plate having a plurality of openings of different sizes, the plate provided in an optical path between the objective lens receiving means and the light detection means, and the openings controlling the quantity of light passing through the plate into the light detection means, the surface inspection method characterized by the steps of observing an abnormal portion of the object to be measured with a naked eye of a user of the surface inspection apparatus while varying an angle in which a difference from a normal portion is observed, selecting a condition of the angle in which the difference from the normal portion can be notably distinguished, and using the selected condition of the angle as an irradiation angle for the light, wherein the illumination switchover means comprises a bright-field/dark-field illumination switchover slide that slides in a direction perpendicular to both an optical axis of a collimate lens for refracting light from the light source applying means and perpendicular to an optical axis of the objective lens receiving means, and along the sliding direction, a circular half-mirror portion for the bright-field illumination and a ring-shaped fully-reflective-mirror portion for the dark-field illumination are provided in parallel with each other, an inner portion of the ring-shaped fully-reflective-mirror portion for the dark-field illumination being a light-pass portion, such that on a periphery of the objective lens receiving means, a ring-shaped dark-field illumination lens is provided, and the ring-shaped dark-field illumination lens is structurally configured such that light reflected on the ring-shaped fully-reflective-mirror portion in a direction of the optical axis of the objective lens receiving means is refracted by the ring-shaped dark-field illumination lens in an oblique direction toward the surface of the object to be measured.

14. The surface inspection method according to claim 13, wherein in the ring-shaped dark-field illumination lens, plural kinds of various refractive indices are provided, and by properly selecting and using the plural kinds of various refractive indices, either the irradiation angle to the surface of the object to be measured or the irradiation angle for the light with respect to the optical axis of the objective lens receiving means can be adjusted.

15. The surface inspection method according to claim 13, wherein the dark-field illumination is employed by the illumination switchover means.

16. The surface inspection method according to claim 13, wherein the light detection means comprises calculation means for converting a light quantity of a light having passed through one of a plurality of openings in the rotatable disc-shaped plate on a basis of a light quantity detected when a standard sample is used as the object to be measured.

17. The surface inspection method according to claim 13, wherein the surface of the object to be measured is irradiated with a light to produce an irradiation light so that the irradiation light is reflected on the surface of the object to be measured to produce a reflected light, and in the reflected light, a component parallel with the optical axis of the objective lens receiving means which is provided at the position opposite to the object to be measured is made incident on the rotatable disc-shaped plate through the objective lens receiving means to produce an incident light, and in the incident light, only a component having passed through one of a plurality of openings of the rotatable disc-shaped plate from the objective lens receiving means is received to produce a received light, and a light quantity of the received light is obtained.

18. The surface inspection method according to claim 17, wherein a light detection extent in the surface of the object to be measured is controlled by changing a size of one of the plurality of openings of the rotatable disc-shaped plate and a magnification of the objective lens receiving means.

19. The surface inspection method according to claim 17, wherein the light quantity of the received light is converted on a basis of a light quantity detected when a standard sample is used as the object to be measured.

20. The surface inspection method according to claim 13, wherein the surface of the object to be measured is irradiated with a light to produce an irradiation light so that the irradiation light is reflected on the surface of the object to be measured to produce a reflected light, and in the reflected light, only a component which is in almost one direction is made incident on the rotatable disc-shaped plate through a tubular member to produce an incident light, and in the incident light, a light quantity of only a component having passed through one of a plurality of openings of the rotatable disc-shaped plate from the tubular member is obtained.

21. The surface inspection method according to claim 20, wherein a light detection extent in the surface of the object to be measured is controlled by changing a size of one of the plurality of openings of the rotatable disc-shaped plate and a magnification of the objective lens receiving means.

22. The surface inspection method according to claim 13, wherein the surface of the object to be measured is irradiated with a light to produce an irradiation light such that the irradiation light is reflected on the surface of the object to be measured to produce a reflected light, and the reflected light is made incident on the rotatable disc-shaped plate through an optical fiber cable to produce an incident light, and in the incident light, a light quantity of only a component having passed through one of the plurality of openings of the rotatable disc-shaped plate through the optical fiber cable is obtained.

23. The surface inspection method according to claim 22, wherein a light detection extent in the surface of the object to be measured is controlled by changing a size of one of the plurality of openings of the rotatable disc-shaped plate and a magnification of the objective lens receiving means.

24. The surface inspection method according to claim 13, wherein the object to be measured is made of a synthetic resin.

25. A method for surface inspection, comprising:
   first steps for naked eye observation, the first steps including:
   (a1) reflecting polarized light off a surface of an object to be measured;
   (b1) observing a portion of the object with the naked eye at various angles;
   (c1) selecting an angle at which a difference from a normal position can be notably distinguished; and
   (d1) using the selected angle as an irradiation angle for light applied to the object;
   second steps, following the first steps, for preservation of objective visual information, the second steps including:
   (a2) if the selected angle equals zero degrees, using bright field illumination, and, if the selected angle equals other than zero degrees, using dark field illumination;
   (b2) passing light reflected off the surface of the object through an objective lens; and
   (c2) passing the reflected light that is incident to the objective lens and parallel to the optical axis of the objective lens through an opening of variable size,
   wherein the configuration of the surface inspection apparatus prevents light that is not incident to the objective lens and parallel to the optical axis of the objective lens from passing through the opening, the opening providing the only path to a light detection member, and the light passing to the light detection member being limited by the size of the opening and chosen magnification of the objective lens, and
   wherein the surface condition of the object is measured with a high degree of accuracy and high correlation to naked eye observation, and the visual information pertaining to the surface condition is preserved via the light detection member.

26. The method as claimed in claim 25, wherein in the second steps the reflected light is passed through an objective lens of less than 10×magnification.

27. The method as claimed in claim 25, wherein in the second steps the reflected light that is incident to the objective lens and parallel to its optical axis is passed through an opening of size ranging from 0.2 to 30 mm.

* * * * *